United States Patent
Tewksbury

(10) Patent No.: US 7,250,265 B2
(45) Date of Patent: Jul. 31, 2007

(54) METHOD OF DETECTING AND EVALUATING ANGIOTENSINOGEN RECEPTOR-MODULATING COMPOUNDS USING PLACENTAL CELLS

(75) Inventor: Duane A. Tewksbury, Marshfield, WI (US)

(73) Assignee: Marshfield Clinic, Marshfield, WI (US)

( * ) Notice: Subject to any disclaimer, the term of this patent is extended or adjusted under 35 U.S.C. 154(b) by 453 days.

(21) Appl. No.: 10/473,668

(22) PCT Filed: Apr. 5, 2002

(86) PCT No.: PCT/US02/10932

§ 371 (c)(1),
(2), (4) Date: Feb. 19, 2004

(87) PCT Pub. No.: WO02/081733

PCT Pub. Date: Oct. 17, 2002

(65) Prior Publication Data

US 2004/0152137 A1    Aug. 5, 2004

Related U.S. Application Data

(60) Provisional application No. 60/282,082, filed on Apr. 6, 2001.

(51) Int. Cl.
*G01N 33/53* (2006.01)
*G01N 33/567* (2006.01)

(52) U.S. Cl. ............. 435/7.21; 436/503; 436/504
(58) Field of Classification Search ........... 435/7.21; 436/503, 504
See application file for complete search history.

(56) References Cited

U.S. PATENT DOCUMENTS 5,595,882 A    1/1997    Fujisawa et al.

OTHER PUBLICATIONS

Petit, A., et al. ; "Angiotensinogen II stimulates both inositol phosphate production and human placental lactogen release from human trophoblastic cells", J. Clinical Endocrinology and Metabolism, 1989, vol. 69, No. 2, pp. 280-286.*
Cell Line Lists, Cell Lines by Tissue Source, ATCC, downloaded Sep. 23, 2006.*

* cited by examiner

*Primary Examiner*—David A. Saunders
(74) *Attorney, Agent, or Firm*—DeWitt Ross & Stevens SC; Charles S. Sara

(57) ABSTRACT

Disclosed is a method of screening a substance for angiotensinogen receptor-modulatory activity. The method includes the steps of contacting placental-derived cells with labeled angiotensinogen and a candidate substance; and then determining whether the candidate substance inhibits the binding of angiotensinogen to the placental-derived cells relative to a control wherein the placental-derived cells are contacted with angiotensinogen in the absence of the candidate substance.

15 Claims, 3 Drawing Sheets

METHOD OF DETECTING AND EVALUATING ANGIOTENSINOGEN RECEPTOR-MODULATING COMPOUNDS USING PLACENTAL CELLS

PRIORITY CLAIM

This is a National Phase application of PCT Application Serial No. PCT/US02/10932, filed 5 Apr. 2002 which claims priority to provisional patent application Ser. No. 60/282,082, filed 6 Apr. 2001, the entire contents of both are incorporated herein by reference.

FIELD OF THE INVENTION

The invention is directed to the revelation of a placenta-specific renin-angiotensinogen receptor system in native human placental cells, and the use of cells exhibiting these newly-revealed receptors to assay putative drug candidates for their ability to modulate binding (reversibly, irreversibly, competitively, or non-competitively) at the placenta-specific renin-angiotensinogen receptor as it is displayed in native human placental cells.

RELATED BACKGROUND

The renin-angiotensin (RA) system is an enzymatic cascade. The first (and rate-controlling) reaction is a renin-catalyzed cleavage of angiotensinogen (AGT) to yield the decapeptide angiotensin I (Ang I). The second step of the cascade is an angiotensin-converting enzyme (ACE)-catalyzed cleavage of Ang I to yield the octapeptide angiotensin II (Ang II). Ang II is the biologically-active component of the RA system.

The concept of a tissue-specific RA system is well established for the adrenal, kidney, and brain. See Racz et al. (1992) *J. Clin. Endocrinol. Metab.* 75:730-737; Tang et al. (1995) *Am. J. Physiol.* 268:F435-F446; and Sernia (1995) *Regul. Pept.* 57:1-18, respectively. In a tissue-specific RA system, all components of the system are produced within that tissue and the components function independently of the circulating RA system. This definition of an "tissue-specific RA system" is explicitly adopted herein. A long-unanswered question has been whether the placenta has a tissue-specific RA system.

It has been well established that the placenta produces substantial amounts of prorenin which could be converted to active renin. ACE is also present in placental tissue. The question, however, of whether AGT is produced by placental tissue has not yet been answered conclusively. Nor has it been established that human placental cells display a renin-angiotensinogen-specific receptor. The mRNA for AGT has been detected in placental tissue. See Sower et al. (1993) *Hypertens. Preg.* 12:163-171 and Cooper et al. (1999) *Placenta* 20:467-474. Also, cDNAs resembling those for kidney-derived AGT receptor proteins have been identified and cloned from placental-derived cDNA libraries. See U.S. Pat. No. 5,595,882, issued 21 Jan. 1997. However, neither the production of the AGT protein itself, nor the identification of a renin-angiotensinogen receptor, has been documented in native human placental cells.

The RA system plays a controlling role in the regulation of blood pressure and aqueous electrolytes in vivo. It also plays a key role in various hypertensive diseases, in congestive heart failure, and in various edematous diseases.

Renin is produced mainly in the kidneys. As noted above, renin cleaves AGT, present in the blood, kidney, and other organs, to produce Ang I. Ang I has very little bioactivity. It is the action of ACE that converts Ang I to Ang II. Ang II is the key bioactive component of the RA system. Another angiotensin, Ang III, is also produced by the human RA system. Ang III is a single amino acid residue shorter than Ang II, and exhibits bioactivity very similar to Ang II.

Significant quantities of AGT have been found in all regions of the placenta, including the amnion and chorion. Haigler et al. (1980) *J. Biol. Chem.* 255:1239-1241. Significant quantities of AGT are also present in amniotic fluid. Tewksbury et al. (1986) *Clin. Chim. Acta.* 158:7-12. However, the predominant form of AGT in all of these sites is a high molecular weight angiotensinogen (HMrA). HMrA has been isolated from placental tissue. Tewksbury (2000) in *Handbook of Physiology. Section 7: The Endocrine System. Vol III: Endocrine Regulation of Water and Electrolyte Balance*, Fray & Goodman (eds) New York, Oxford University Press, pp 59-80. There are five distinct forms, all of which are multimers of the normally occurring low molecular weight angiotensinogen (LMrA). HMrA also occurs in the plasma of pregnant women, accounting for 16% of the total AGT in the latter half of pregnancy. Forty-seven percent of women who develop pregnancy induced hypertension (PIH) have significantly elevated levels of plasma HMrA. See Tewksbury et al. (1982) *Hypertension* 4:729-734; and Tewksbury et al. (1988) in *Placental and Endometrial Proteins: Basic and Clinical Aspects*, Utrecht, VSP, pp 651-654.

The most important biological activity of Ang II is its powerful vasoconstrictive effect, especially in the peripheral blood vessels. This action is critical to maintaining proper blood pressure. Arg II is also known to induce the adrenal zone glomerulosa to produce aldosterone. Ang II also is known to act on the adrenal medulla and sympathetic nerve ends to promote catecholamine secretion, vasopressin secretion, and prostaglandin E2 and I2 production. Due to its wide-ranging biological activity, investigations of pharmaceutically-active compounds that interfere with or otherwise modulate the intersection of Ang II with the rest of the RA systems have been many.

For example, "β-blockers" are a class of compounds known to inhibit renin production, renin being the rate-limiting enzyme in the cascade leading from angiotensinogen to Ang II. However, because β-blockers do not act upon a single receptor type, focus has shifted in recent years to a search for compounds that, rather than inhibiting the production of renin, inhibit the action of the renin enzyme itself. There have also been many pharmaceutical agents successfully launched that are ACE inhibitors, such as captopril (1-{(2S)-3-mercapto-2-methylpropionyl}-L-proline), enalapril ((S)-1-{N-[1-(ethoxycarbonyl)-3-phenylpropyl-L-alanyl}-L-proline-(Z)-2-butenedioate), delapril (N-{N-{(S)-1-ethoxycarbonyl-3-phenylpropyl}-L-alanyl}-N-(indal-2-yl) glycine hydrochloride) and alacepril (1-{(S)-3-acethylthio-2-methylpropanoyl}-L-propyl-L-phenylalanine). These drugs are used to treat essential and/or renovascular hypertension. Although these drugs (and many other ACE-inhibitors) are already in commercial use, they have undesirable side effects. Therefore, investigations continue into developing an Ang II receptor antagonist that more specifically suppresses only Ang II bioactivity.

High-throughput screening of candidate compounds is therefore a key concern of the pharmaceutical industry. Developing efficacious pharmaceutical agents requires a means to screen myriad candidate compounds for activity against a RA system receptor. Only those candidate compounds that pass the initial screening are advanced to far more expensive animal testing. Moreover, the initial screening approach should mimic, as closely as possible, the ultimate animal response, e.g., the human response, to the drug candidate being evaluated. Therefore, to assess the modulator activity of a human drug candidate, it is preferred to use human cells that have Ang II receptors (as opposed to using membrane fractions or cells derived from laboratory animals).

SUMMARY OF THE INVENTION

The present inventor postulated that there is an intact, tissue-specific placental RA system that utilizes circulating AGT as the AGT source. This postulate implies that there must be a specific uptake of AGT in the placental cells. This specific uptake would thus require an AGT-specific receptor on the placental cells. The present invention confirms the existence of such a receptor and includes using the receptor as a means to evaluate potential drug candidates for their modulatory effect on the receptors.

Thus, the present invention is directed to a method of screening a substance for AGT receptor-modulatory activity. Here, the method comprises simultaneously contacting placental-derived cells with labeled AGT and a candidate substance, and then determining whether the candidate substance inhibits the binding of AGT to the placental-derived cells relative to a control wherein the placental-derived cells are contacted with AGT in the absence of the candidate substance.

More specifically, a second embodiment of the invention is directed to a method of screening a substance for AGT receptor-modulatory activity comprising first contacting cells with labeled AGT, whereby an amount of the AGT binds to the cells. The amount of labeled AGT that binds to the cells is then measured. The cells are then contacted with a candidate substance and amount of labeled AGT that is displaced from the cells is determined. In this fashion, the receptor-modulatory activity of the candidate substance, if any, is revealed by its ability to displace AGT from the cell surface.

Yet another embodiment of the invention is directed to a method of screening a substance for AGT receptor-modulatory activity comprising contacting a first plurality of cells with labeled AGT, whereby an amount of the AGT binds to the cells; then measuring the amount of labeled AGT that binds to the cells over time; and then fabricating a standard curve indicating the amount of AGT that binds to the first plurality of cells over time. The standard curve can then be used as a tool to evaluate candidate substances that interfere with AGT binding. Thus, a second plurality of cells of the type used to make the standard curve is contacted with a candidate substance, under the same conditions as used to generate the standard curve. The second plurality of cells is then contacted with labeled AGT, whereby an amount of the AGT binds to the cells. The amount of labeled AGT that binds to the second plurality of cells is then determined and compared to the corresponding amount to the standard curve previously generated. In this fashion, the receptor-modulatory activity of the candidate substance, if any, is revealed.

The subject invention has many advantages, the foremost being that it is conducted using placental cells, preferably human placental cells. Because the method preferably uses human cells, it yields results that should carry over into corresponding results in vivo. These and other advantages of the present invention will become apparent upon a complete reading of the detailed description, examples, and claims.

DETAILED DESCRIPTION

Figure 1:
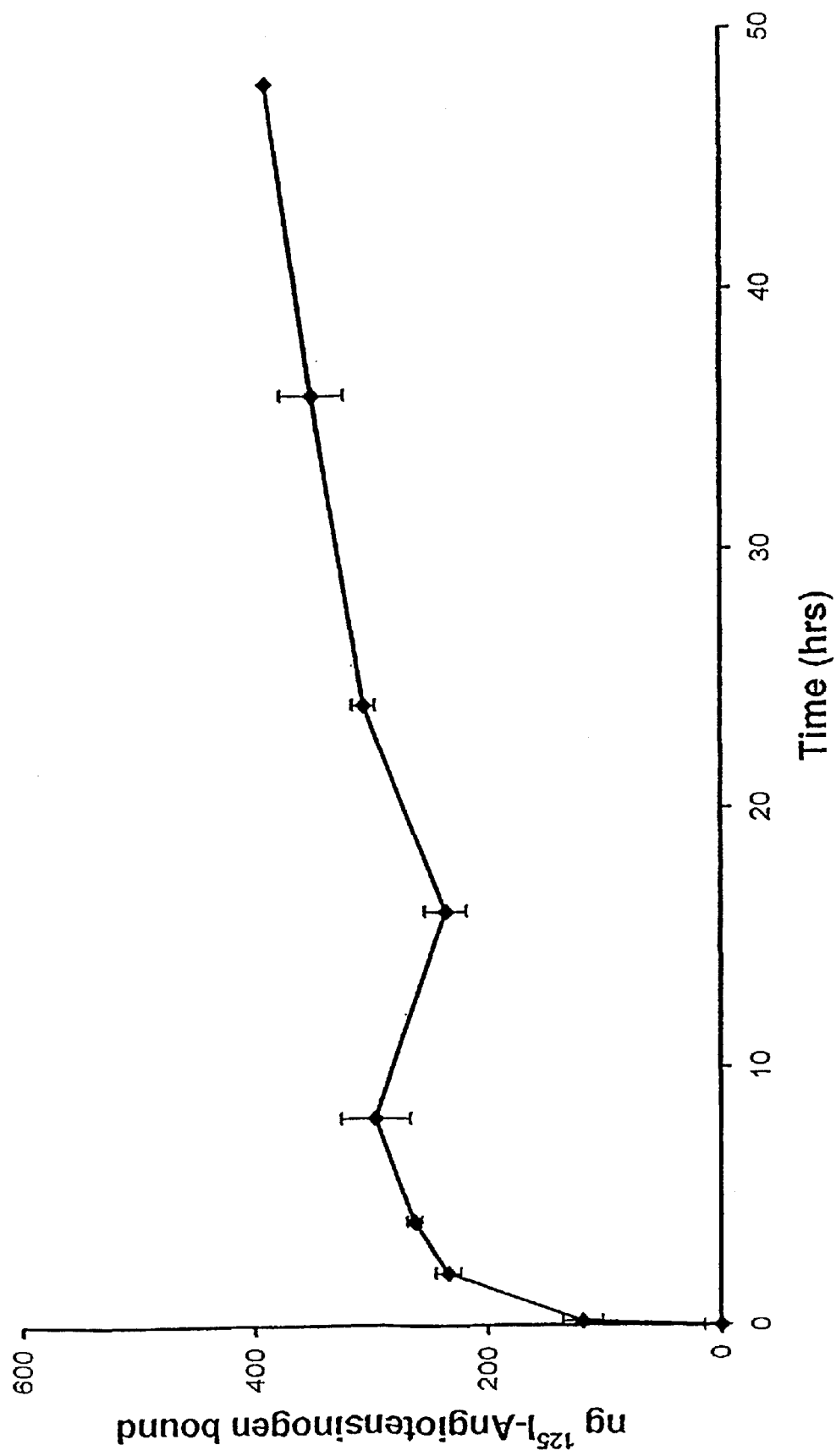
FIG. 1: Binding of $^{125}$I-labeled AGT by placental-derived cells. Each point represents the mean ±2 SD of two experiments, each of which contained two duplicates. See Example 1.

As described in the Examples, below, the present invention has shown that there exists a tissue-specific AGT receptor that is exhibited on placental-derived cells. There are at least three possible functions for the AGT receptor on these cells. First, the receptor could be immobilizing AGT at a specific site so as to facilitate reaction with renin. The entire RA system could be functioning at or near this site, thus facilitating the release of Ang II in the vicinity of its receptor. Second, the binding of AGT to the receptor could initiate a signaling process that would affect the internal function of the cell, such as the production of renin. Third, the cell could internalize the AGT-receptor complex, as the Examples strongly indicate, with dissociation of the complex occurring in the lysosome. The released AGT could participate in an intracellular RA system or other intracellular biochemical pathway.

The working hypothesis of the inventor is that the placental RA system utilizes LMrA that has been taken up from circulating blood and that there is a mechanism for multimerization of LMrA to form HMrA. In times of abnormal function of the placental-fetal unit, the placents can increase the production of HMrA which would decrease the reaction of renin with its substrate, thus attenuating the placental RA system and its resulting vasoconstricting activity. If the AGT receptor is an integral component of the placental RA system, then the attentuation of the placental RA system can be more clearly understood. Seven or more molecular of LMrA are used to form one molecule of HMrA. Thus the number of molecules of LMrA available to react with the AGT receptor is reduced by a factor of seven or more, resulting in the attenuation of the placental RA system. It is not known if HMrA binds to the AGT receptor, but the above argument is valid in either case.

The ultimate purpose and underlying biochemical phenomena that drive the placenta-specific RA system, however, are not critical to an understanding of the present invention. The present inventor disavows any such knowledge, nor is any such knowledge required to practice the present invention. Nor is the present invention limited by the above discussion regarding the mechanistic aspects of the placental RA system. All that is required to practice the present invention is the information provided herein, coupled with the knowledge (also revealed herein) that placental cells exhibit a receptor that binds AGT specifically. These receptors can therefore be utilized to screen candidate substances for their ability, if any, to modulate the interaction of AGT with the placenta-specific AGT receptor.

Thus, in its broadest embodiment, the present invention is directed to a method of screening a substance for AGT receptor-modulatory activity. The method comprises simultaneously contacting cells with labeled AGT and a candidate substance and then determining whether the candidate substance inhibits the binding of AGT to the cells relative to a control wherein the cells are contacted with AGT in the absence of the candidate substance. The comparison between the test run and the control run is most conveniently accomplished by way of a standard curve constructed by exposing cells to various levels of AGT over time and measuring the amount of AGT that binds to the cells.

The AGT may be labeled by any means known to the art or developed in the future for labeling a chemical moiety (a polypeptide moiety in particular). Thus, the label may be a radioactive label, such as the $^{125}$I described in the Examples, $^{32}$P, $^{14}$C, $^{3}$H, and the like. The label can also be a fluorophore, such as dansyl, rhodamine, fluorescein, tetramethylrhodamine, resazurin, etc. A very large number of suitable fluorophores are known in the art and available commercially from such entities as Molecular Probes, Inc. (Eugene, Oreg.). The label may also be detectible colorimetrically, as by a dye such as resazurin, alamarBlue, and tetrazolium-based dyes such as MTT, XTT, MTS, INT, and the like. All of these dyes can be purchased commercially from a number of sources (e.g., Aldrich Chemical, Milwaukee Wis.; Promega Corp., Madison, Wis., and Molecular Probes). $^{125}$I-labeled Ang II is available commercially from Amersham Biosciences AB (Uppsala, Sweden).

The placental cells to be used in the method can be placental cells from any mammalian source, without limitation. Human placental cells are preferred. A wide variety of cultured placental cells (human, rat, murine, bovine, feline, etc.) can be purchased commercially from the American Type Culture Collection (ATCC), Manassas, Va. The ATCC also provides suggested culture conditions for all of the cell types it offers. Preferred human placental cell lines include those deposited with the ATCC under accession numbers CRL-7548, CRL-7458, and CRL-7459.

The nature of the candidate substance to be tested according to the present invention is not critical. Thus, any drug candidate, suspected drug candidate, or any other substance, compound, element, etc. may be tested for its ability to modulate the placenta-specific AGT-receptor using the present invention.

In one aspect of the invention, a substance is tested for its ability to displace AGT from the placenta-specific receptors. Here, the method comprises first contacting placental-derived cells with labeled AGT, whereby an amount of the AGT binds to the cells. This is a baseline of AGT binding in the absence of the candidate substance to be tested (See Example 1). The amount of labeled AGT that binds to the cells is then determined (using the signal generated by the label). The cells are then contacted with the candidate substance. If the substance is capable of displacing AGT from the surface of the cells, the signal from the label on the AGT will appear in the supernatant. Thus, the amount of labeled AGT that is displaced from the cells is determined, whereby the receptor-modulatory activity of the candidate substance, if any, is revealed.

In another aspect of the invention, the opposite competitive activity is determined, that is, the ability of AGT to displace a candidate substance from the receptors. In this approach, a standard curve for AGT binding is constructed. Thus, a first plurality of placental-derived cells is contacted with labeled AGT, whereby an amount of the AGT binds to the cells. The amount of labeled AGT that binds to the cells over time is measured, and a standard curve indicating the amount of AGT that binds to the first plurality of cells over time is constructed.

To evaluate the candidate substance, a second plurality of placental-derived cells of the type used to construct the standard curve (and under the same conditions) is contacted with a candidate substance. The cells are then contacted with labeled AGT, whereby an amount of the AGT binds to the cells. The amount of labeled AGT that binds to the second plurality of cells is then compared to the corresponding value on the standard curve generated previously. Any attenuation in the amount of AGT binding indicates that the candidate substance being evaluated has occupied the AGT receptors on the cells.

The Examples that follow provide a more detailed description of the invention.

EXAMPLES

The following Examples are included solely to provide a more complete and consistent understanding of the invention disclosed and claimed herein. The Examples do not limit the scope of the invention in any fashion.

General Procedures for All Examples

Cell Culture: CRL-7548 placental cells obtained from American Type Culture Collection were cultured in 89% Dulbecco's modification of Eagle medium (DEME) (Cellgro, Herndon, Va.), 10% fetal bovine serum (FBS) (Sigma, St. Louis, Mo.), 1% penicillin-streptomycin (5,000 U/ml and 5,000 µg/ml) (Cellgro) in a humidified atmosphere of 5.0% $CO_2$ and 95% $O_2$ at 37° C. The cells were passed in FBS-free DEME before experimentation, seeded in 35 mm diameter plastic wells and cultured for two days to reach about 80-90% confluence.

AGT:

The AGT used in the Examples was purified from human plasma as described in Tewksbury (1983) *Fed. Proc.* 42:2724-2728; and Tewksbury et al. (1981) *Biochem. Biophys. Res. Commun.* 99:1311-1315. The specific Ang I content was 20 µg Ang I/mg protein. The theoretical value is 21 µg Ang I/mg protein. The preparation exhibited the usual double-banded pattern on sodium dodecyl sulfate-polyacrylamide gel electrophoresis (SDS-PAGE) with no other proteins being apparent.

$^{125}$I -Labed AGT:

Purified AGT was labeled with $^{125}$I using iodobeads Pierce, Rockford, Ill.), 5 mCi/0.5 mg AGT in 0.1 mol/L sodium phosphate buffer, pH 6.0. The bound isotope was separated from the free isotope by gel filtration on Sephadex G-25.

Example 1

AGT Binding

Labeled AGT, 3 µg, was added to each well containing 1 ml DEME and 2-3×10$^4$ cells. The cells were harvested at 5 min, and 2, 4, 8, 16 and 24 h, washed five times with DEME, lysed in a buffer containing 0.1 mol/L Tris, 2 mmol/L EDTA, 1% Triton-X 100, 1 µmol/L DTT, pH 7.8, and the radioactivity of the whole lysate measured. Each experiment contained two duplicates and the reported values are the mean of two experiments. The results are presented graphically in FIG. 1

Example 2

Competitive Binding Study

This Example was carried out as described in Example 1, except that a 100-fold excess of unlabeled AGT was added at zero time. The cells were harvested at 5 min, and 4, 8 and 24 h. The results are presented graphically in FIG. 2

Example 3

Competitive Displacement Study

This Example was carried out as described in Example 1, except that at 8 h, a 200-fold excess of unlabeled AGT was added to duplicate wells. The cells were harvested at 5 min and at 2 intervals through 18 h.

Example 4

Acid Wash Study

This Example was carried out as described in Example 1. At 8 h, the cells in one set of duplicate wells were washed five times with DEME. Another set of duplicate samples were incubated with 0.2 mol/L acetic acid, 0.5 mol/L NaCl, pH 2.5, on ice (4° C.) for 6 min, and then washed five times with the acid wash. The control duplicates and the acid-washed duplicates were lysed and radioactivity was measured.

The results showed that an acetic acid wash at 4° C. removed 46% of the bound AGT from the cells, thus indicating that about half of the bound AGT had been internalized by the cells. This Example shows that not only do the placental cells have an AGT-specific receptor, the cells internalize at least a portion of the AGT bound to the receptor.

Example 5

AGT Uptake in Other Placental Cell Lines

The cells used in Examples 1-4 are fibroblasts originally derived from a human placenta obtained at 5 months gestation. Binding studies were also done with fibroblasts derived from a human placenta obtained at 37 weeks gestation (CRL-7458) and with fibroblasts derived from a human placenta at 40 weeks gestation (CRL-7459). These cells also took up AGT.

Results and Conclusions from Examples 1-5

Figure 2:
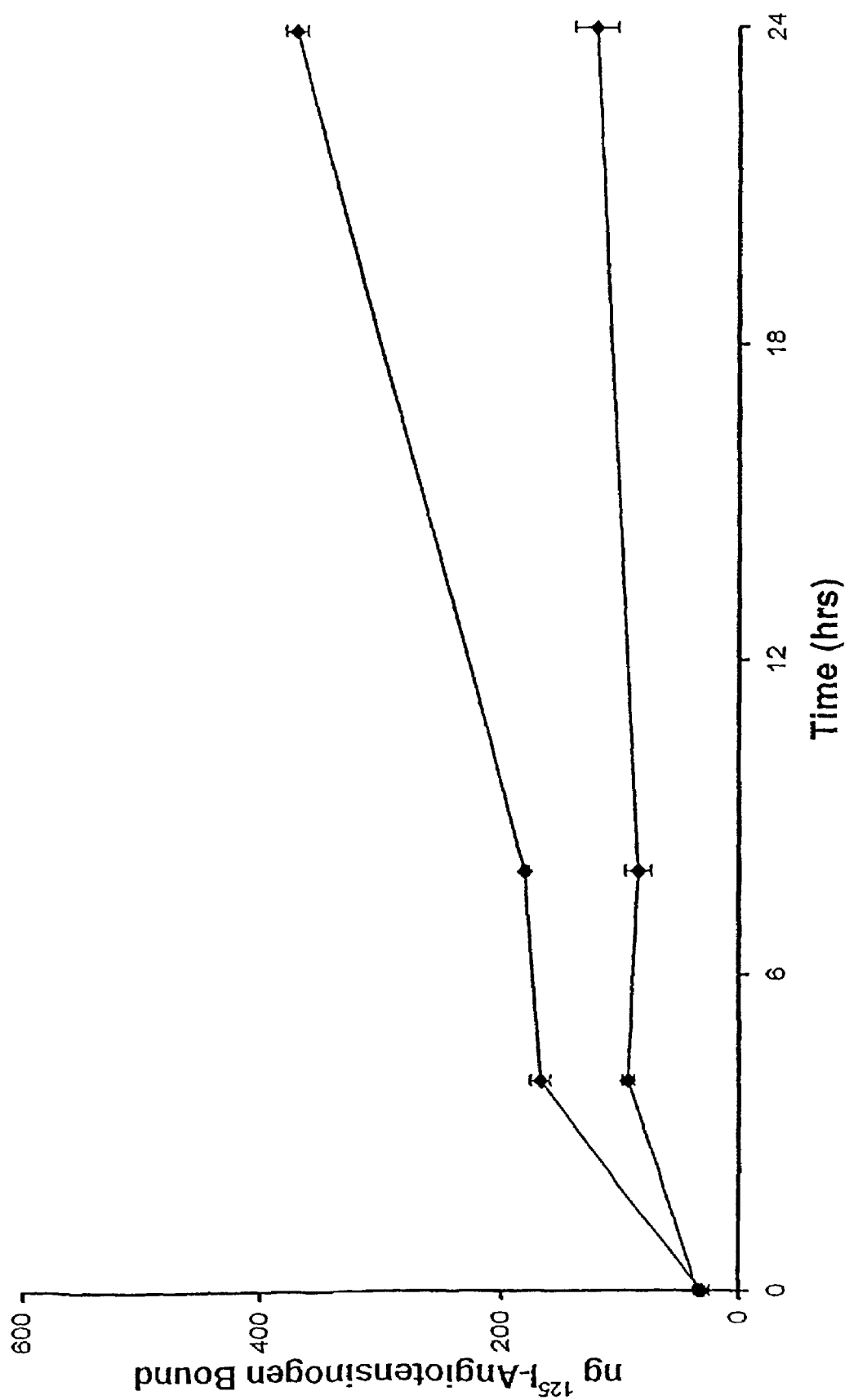
FIG. 2: Competitive inhibition of binding of $^{125}$I-labeled AGT by placental-derived cells by unlabeled AGT. The top line represents the control binding. The bottom line represents the binding in the presence of a 100-fold excess of unlabeled AGT. Each point represents the mean ±2 SD of two experiments, each of which contained two duplicates. See Example 2.

As clearly shown in FIG. 1 (which depicts the results of Example 1), the placental-derived cells rapidly bound $^{125}$I-AGT in a time-dependent manner, with saturation being achieved in 2-4 h. As shown in FIG. 1, the binding of AGT by these cells is time-dependent. As shown by FIG. 2 (which depicts the results of Example 2), this binding was competitively inhibited by unlabeled AGT. Prior addition of a 100-fold excess of unlabeled AGT resulted in a 54% decrease in maximal binding.

Figure 3:
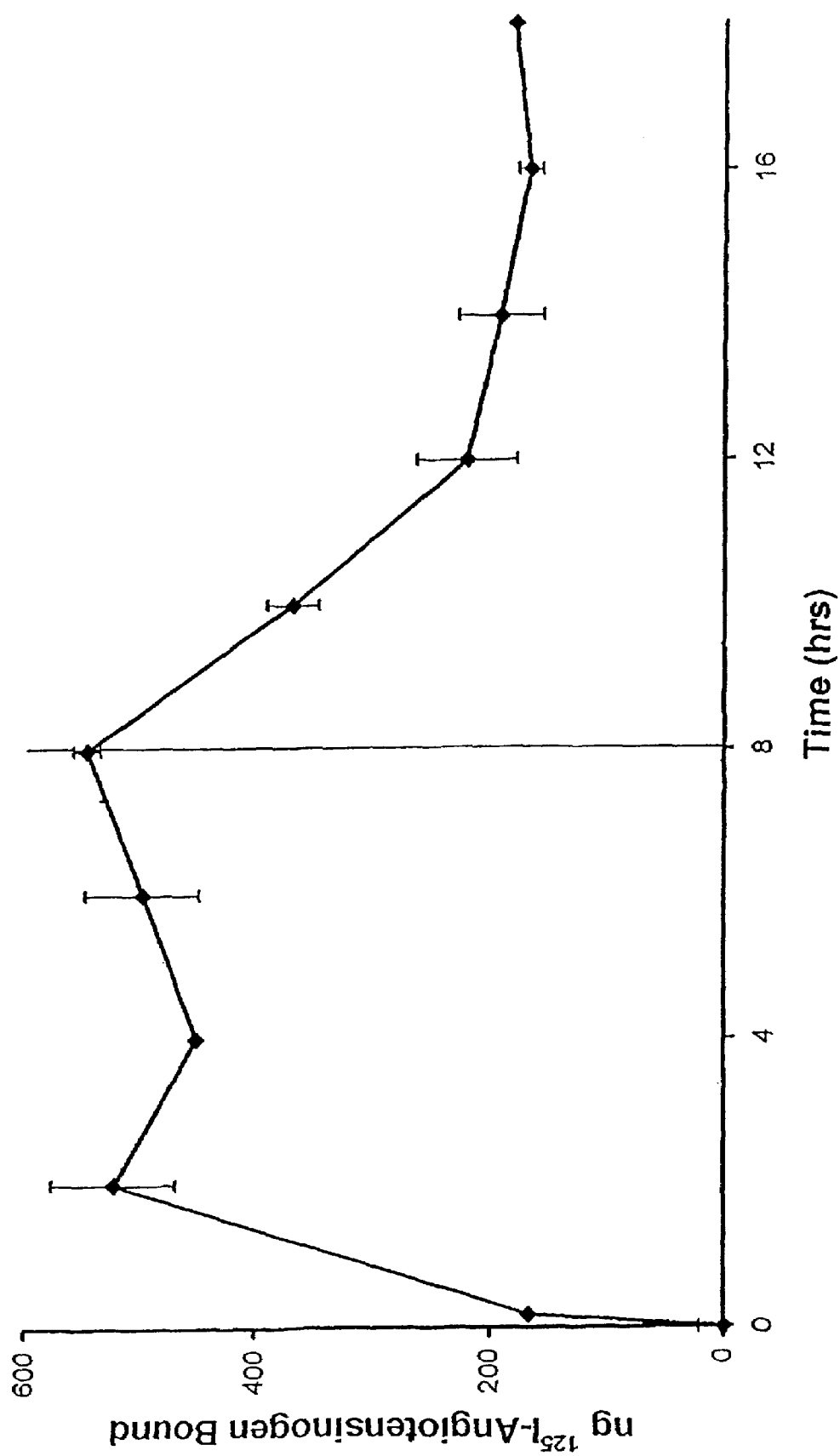
FIG. 3: Competitive displacement of $^{125}$I-labeled AGT bound to placental-derived cells by unlabeled AGT. At 8 h a 200-fold excess of unlabeled AGT was added to the cells. Each point represents the mean ±2 SD of two experiments, each of which contained two duplicates. See Example 3.

Bound AGT was also competitively displaced by AGT. See FIG. 3, which depicts the results of Example 3. Adding a 100-fold excess of unlabeled AGT displaced 70% of the bound $^{125}$I-AGT. Thus, approximately 30% of the total binding can be attributed to nonspecific binding, while 70% of the AGT bound to an AGT-specific receptor. This type of displacement is typically seen with a receptor directed towards a specific ligand.

An acid wash (0.2 mol/L acetic acid, 0.5 mol/L NaCl, pH 2.5) at 4° C. (Example 4) removed 46% of the bound $^{125}$I-AGT. An acid wash is known to dissociate cell surface ligand-receptor complexes, but does not remove internalized ligand. Ligand-receptor complexes are dissociated at low pH. It has been shown previously that the acetic acid wash used in the Example 4 removes cell surface-bound ligands, but does not remove the internalized ligand. See Haigler et al. (1980) *J. Biol. Chem.* 255:1239-1241. Thus, Example 4 shows that the placental cells internalized at least a portion of the AGT bound to the receptor.

Example 5 shows that the binding of AGT is not limited to CRL-7548 placental cells (20 weeks gestation), but is also exhibited by other placental cell types, including CRL-7458 (37 weeks gestation) and CRL-7459 (40 weeks gestation). The significance of this Example is that the three placental cell types tested span a considerable portion of the gestational time period in humans. Thus, these placental cell lines can be used to assay during candidate compounds for their potential to inhibit AGT uptake in placental cells.

Overall, these results indicate the existence of an AGT receptor on placental-derived cells. It also reveals the proportion of AGT molecules that bind to the receptor and which are then subsequently imported into the cells themselves can be determined. Thus, disruption or modulation of this receptor uptake system can be used as a means to evaluate drug candidates for their ability to act as AGT-uptake inhibitors.

Example 6

Competitive Displacement of Labeled AGT By Candidate Substance

In this Example, the AGT receptor-modulatory activity of a candidate substance will be evaluated by determining its ability to displace labeled AGT previously bound to placental-derived cells.

Placental-derived cells are contacted with $^{125}$I-labeled AGT as described in Example 1. The cells are then contacted with a candidate substance, such as a putative AGT agonist or antagonist. The amount of labeled AGT that is displaced from the cells is then determined by measuring the supernatant for the amount of displaced $^{125}$I radioactivity. This reveals how much of the labeled AGT is displaced from the surface of the cells by the action of the candidate substance.

Example 7

Competitive Displacement of Candidate Substance by Labeled AGT

This Example proceeds in the same fashion as Example 6, with the exception that the cells are first contacted with the candidate substance for a period of time and under suitable conditions whereby the candidate substance is able to bind to the surface of the cells. The cells are then contacted with labeled AGT, whereby an amount of the AGT binds to the cells, displacing the candidate substance. Any attenuation of the amount of AGT that binds to the cell surface, as compared to a control performed as described in Example 1, indicates modulatory activity in the candidate substance.

What is claimed is:

1. A method of screening a substance for angiotensinogen receptor-modulatory activity, the method comprising:
   (a) contacting placental-derived cells with labeled angiotensinogen, whereby an amount of the angiotensinogen binds to the cells; then
   (b) measuring the amount of labeled angiotensinogen from step (a) that binds to the cells; then
   (c) contacting the cells from step (b) with a candidate substance; and then
   (d) measuring an amount of labeled angiotensinogen that is displaced from the cells of step (c), whereby the receptor-modulatory activity of the candidate substance, if any, is revealed.

2. The method of claim 1, wherein in step (a), human placental-derived cells are contacted with labeled angiotensinogen.

3. The method of claim 1, wherein in step (a), human placental-derived cells from the cell line CRL-7548 are contacted with the labeled angiotensinogen.

4. The method of claim 1, wherein in step (a), the labeled angiotensinogen is labeled with a label selected from the group consisting of radioactive labels, fluorescent labels, and colorimetric labels.

5. The method of claim 1, wherein in step (a), the labeled angiotensinogen is labeled with $^{125}$I.

6. A method of screening a substance for angiotensinogen receptor-modulatory activity, the method comprising:
   (a)
      i. contacting a first plurality of placental-derived cells with labeled angiotensinogen, whereby an amount of the angiotensinogen binds to the cells; then
      ii. measuring the amount of labeled angiotensinogen that binds to the cells over time; and then
      iii. generating a standard curve indicating the amount of angiotensinogen that binds to the first plurality of cells over time; and
   (b) contacting a second plurality of placental-derived cells of the type used in step (a), under the same conditions as in step (a), with a candidate substance; then
   (c) contacting the second plurality of cells from step (b) with labeled angiotensinogen, whereby an amount of the angiotensinogen binds to the cells; then
   (d)
      i. measuring the amount of labeled angiotensinogen from step (c) that binds to the second plurality of cells; and
      ii. comparing the amount to the standard curve generated in step (a), whereby the receptor-modulatory activity of the candidate substance, if any, is revealed.

7. The method of claim 6, wherein the first and second pluralities of placental-derived cells are human placental-derived cells.

8. The method of claim 6, wherein the first and second pluralities of placental-derived cells are human placental-derived cells from the cell line CRL-7548.

9. The method of claim 6, wherein the labeled angiotensinogen is labeled with a label selected from the group consisting of radioactive labels, fluorescent labels, and colorimetric labels.

10. The method of claim 6, wherein the labeled angiotensinogen is labeled with $^{125}$I.

11. A method of screening a substance for angiotensinogen receptor-modulatory activity, the method comprising:
    (a) simultaneously contacting placental-derived cells with labeled angiotensinogen and a candidate substance; and then
    (b) determining whether the candidate substance inhibits the binding of angiotensinogen to the placental-derived cells relative to a control wherein the placental-derived cells are contacted with angiotensinogen in the absence of the candidate substance, whereby the receptor-modulatory activity of the candidate substance, if any, is revealed.

12. The method of claim 11, wherein in step (a), human placental-derived cells are contacted with labeled angiotensinogen and the candidate substance.

13. The method of claim 11, wherein in step (a), human placental-derived cells from the cell line CRL-7548 are contacted with labeled angiotensinogen and the candidate substance.

14. The method of claim 11, wherein in step (a), the labeled angiotensinogen is labeled with a label selected from the group consisting of radioactive labels, fluorescent labels, and colorimetric labels.

15. The method of claim 11, wherein in step (a), the labeled angiotensinogen is labeled with $^{125}$I.

* * * * *